(12) United States Patent
Blair

(10) Patent No.: US 6,506,791 B2
(45) Date of Patent: Jan. 14, 2003

(54) METHOD OF TREATMENT OF PROTOZOAN INFECTIONS IN FISH

(75) Inventor: Benjamin G. Blair, Ohatchee, AL (US)

(73) Assignee: Jacksonville State University, Jacksonville, AL (US)

( * ) Notice: Subject to any disclaimer, the term of this patent is extended or adjusted under 35 U.S.C. 154(b) by 0 days.

(21) Appl. No.: 09/922,403

(22) Filed: Aug. 3, 2001

(65) Prior Publication Data

US 2002/0037921 A1 Mar. 28, 2002

Related U.S. Application Data

(60) Provisional application No. 60/223,915, filed on Aug. 9, 2000.

(51) Int. Cl.$^7$ ............................ A61K 31/35; A61N 1/30
(52) U.S. Cl. ......................................... 514/454; 604/20
(58) Field of Search ............................. 514/454; 604/20

(56) References Cited

PUBLICATIONS

N. Houba–Herin et al.; Mechanisms for Dye–Mediated Photodynamic Action: Singlet Oxygen Production Deoxyguanosine and Phage Inactivating Efficiencies; Photochem Photobiol.; 1982; pp. 297–306; vol 36; Pergamon Press Ltd., Great Britain.
Heitz, James R.; Pesticidal Applications of Halogenated Xanthene Molecules; Light Activated Pest Control; 1995; pp. 1–15; American Chemical Society, Washington, D.C..
Heitz, James Robert, Pesticidal Applications of Halogenated Xanthene Dyes; Phytoparasitica, Israel Journal of Plant Protection Sciences; Apr. 1997; pp. 88–92; vol. 25, No. 2; Priel Publishers, Israel..
Hatch, Audrey C. and Burton, Allen; Effects of Photoinduced Toxicity of Fluoranthene on Fluoranthene on Amphibian Embryos and Larvae; Environmental Toxicology and Chemistry; 1988; pp. 1777–1785; vol. 17, No. 9; Setac Press, USA.
Chase, Victor, Waiter! There's a Dye in My Soup; Innovations; Feb. 1996; pp. 156–16; vol. 104, No. 2; Environmental Health Perspectives, http://ehpnetl.niehs.nih.gov/docs/1996/104–2/innov.html; Research Triangle Park, NC.
Carpenter, Terry L. and Heitz, James, R., Light–Dependent Latent Toxicity of Rose Bengal to Culex pipiens Quinquefasciatus; Environ. Entomol; 1980; pp. 533–537; vol. 9; No. 5 Entomological Society of American, USA.
Carpenter, Terry L. et al., Acute Light–dependent Toxicity of Free–acid Formulations of Xanthene Dyes to Larval Culex quinquefasciatus Say (Diptera: Culicidae); Environ. Entomol.; 1984; pp. 1366–1370; vol. 13.
Alcantara–Licudine, Jocelyn P. et al.; Analysis of Phloxine B and Uranine in Coffee by High–Performance Liquid Chromatography and Capillary Zone Electrophoresis After Solid Phase Extraction Cleanup; J. Agric. Food Chem.; 1998; pp. 1005–1011; vol. 46; American Chemical Society, USA.

Alcantara–Licudine, Jocelyn P. et al.; Method for the Analysis of Phloxine B, Uranine, and Related Xanthene Dyes in Soil Using Supercritical Fluid Extraction and High–Performance Liquid Chromatography; J. Agric. Food. Chem.; 1997; pp. 766–773; vol. 45; American Chemical Society, USA.
Zarain–Herzberg, Martha et al., Taura Syndrome in Mexico: Follow–Up Study in Shrimp Farms of Sinaloa: Aquaculture; 2001; pp. 1–9; vol. 193; Elsevier Science B.V.
Walthali, W.K. and Stark, J.D., The Acute and Chronic Toxicity of Two Xanthene Dyes, Fluorescein Sodium Salt and Phloxine B, to *Daphnia pulex*, Environmental Pollution; 1999; pp. 207–215, vol. 104; Elsevier Science Ltd..
Lee, Plato C.C. and Rodgers, Michael A.J., Laser Flash Photokinetic Studies of Rose Bengal Sensitized Photodynamic Interactions of Nucleotides and DNA, Photochemistry and Photobiology 1987; pp. 79–86 vol. 45, No. 1, Pergamon Journals Ltd.
Knox, J.P. and Dodge, A.D., The Photodynamic Action of Eosin, a Singlet–Oxygen Generator, Planta, 1985, pp. 22–29, vol. 164, Springer–Verlag.
Schroder, Robert F. et al., Evaluation of a Water–Soluble Bait for Corn Rootworm (Coleoptera: Chrysomelidae) Control. J. Entimol. Sci., Jan. 29, 1998, pp. 355–364, vol. 33, No. 4.
Liquido, Nicanor J. et al., Light–Activated Toxicity of Phloxine B and Fluorescein in Methyleugenol to Oriental Fruit Fly, *Bactrocera dorsalis* (Hendel) (Diptera: Tephritidae), Males, Light Activated Pest Control., 1995, pp. 107–111, Chapter 8, American Chemical Society.
Mangan, Robert L. and Moreno, Daniel S., Development of Phloxine B and Uranine Bait for Control of Mexican Fruit Fly, Light Activated Pest Control, 1995, p. 15, Chapter 9, American Chemical Society.
Liquido, Nicanor J. et al., Light–Activated Toxicity of Phloxine B and Uranine to Mediterranean Fruit Fly, *Ceratitis Capitata* (Wiedemann) (Diptera: Tephritidae), Adults, Light Activated Pest Control, 1995, pp. 82–104, Chapter 7, American Chemical Society.
Lipman, Arthur L., Safety of Xanthene Dyes According to the U.S. Food and Drug Administration, Light Activated Pest Control, 1995, pp. 34–53, Chapter 4, American Chemical Society.
Bender, J. Voisinet and Licudine, J.P. Alcantra, Dissipation of Phloxine B and Uranine in Sediment and Water at a Kauai Spill Site, Bull Environ Contam. Toxicol., 1998, pp. 426–432, vol. 61, Springer–Verlag, New York.
Li, Qing X. et al., Determination of Phloxine B and Uranine in Water by Capillary Zone Electrophoresis, Journal of Chromatographic Science, Dec. 1997, pp. 573–577, vol. 35, Dec. 1997.

(List continued on next page.)

Primary Examiner—Rebecca Cook
(74) Attorney, Agent, or Firm—Alston & Bird LLP

(57) ABSTRACT

A method of treating protozoan infections in fish comprising introducing a sufficient quantity of one or more photoactive dyes to an aqueous environment containing one or more fish infected with protozoa such that the resulting concentration of the one or more photoactive dyes in the aqueous environment is toxic to at least some of the protozoa.

18 Claims, 1 Drawing Sheet

OTHER PUBLICATIONS

Fort, Douglas J. et al., Ecological Hazard Assessment of Aqueous Soil Extracts Using FETAX, Journal of Applied Toxicology, 1995, pp. 183–191, vol. 15, John Wiley & Sons, Ltd.

Dresser, Todd H. et al., Teratogenic Assessment of Four Solvents Using the Frog Embryo Teratogenesis Assay–Xenopus (FETAX), Journal of Applied Toxicology, 1992, pp. 49–55, John Wiley & Sons, Ltd.

Rayburn, James R. et al., Developmental Toxicity of Copper Chloride, Methylene Chloride, and 6–Amininicotinamide to Embryos of the Grass Shrimp Palaemonetes Pugio, Environmental Toxicology and Chemistry, 1999, pp. 950–957, vol. 18, No. 5, pp. 950–957, Setac Press, USA.

Heitz, James R. Development of Photoactivated Compounds as Pesicides, Light Activated Pesticides, 1987, pp. 1–21, Chapter 1, American Chemical Society.

Wu, Jun et al., Capillary Zone Electrophoretic Determination of Heterocyclic Aromatic Amines in Rain, Journal of Chromatographic Science, Dec. 1995, pp. 712–716, vol. 33.

Willeford, Kenneth O. et al., Efficacy of Phloxine B as a Bactericidal Agent in Plants, J. Agric. Food Chem., 1998, pp. 1637–1641, vol. 46, American Chemical Society.

Wang, L. et al., Photolysis of Phloxine B in Water and Aqueous Solutions, Archives of Environmental Contamination and Toxicology, 1998, pp. 397–403, vol. 35, Springer–Verlag New York, Inc.

Walthali, W.K. and Stark, J.D., The Acute and Chronic Toxicology of Two Xanthene Dyes, Fluorescein Sodium Salt and Phloxine B, to Daphnia Pulex, Environmental Pollution, 1999, pp. 207–215, vol. 104, Elsevier Science Ltd.

Tsekos, I. et al., Microspectrophotometric Analysis of Accumulation of the Fluorones K–Fluorescein, Rose Bengal and Phloxine Red in Living Plant Cells, Biotechnic & Histochemistry, 1997, pp. 304–314, vol. 7(6).

Lutty, Gerard A., The Acute Intravenous Toxicity of Biological Stains, Dyes and Other Fluorescent Substances, Toxicology and Applied Pharmacology, 1978, pp. 225–249, vol. 44, Academic Press.

Wagner, Stephen, Effects of Acridine Plus Near Ultraviolet Light on *Escherichia coli* Membranes and DNA in Vivo, Photochemistry and Photobiology, 1980 pp. 771–779, vol. 32, Pergamon Press Ltd., Great Britain.

Ito, Takashi and Kobayashi, Katsumi, A Survey of In Vivo Photodynamic Activity of Xanthenes, Thiazines, and Acridines in Yeast Cells, Photochemistry and Photobiology, 1977, pp. 581–587, vol. 26.

Carpenter, Terry L. and Heitz, James R., Light–Dependent and Independent Toxicity of Erythrosin B to Culex Pipiens Quinquefasciatus Say, Environmental Entomology, 1981, pp. 972–976, vol. 10, No. 6.

Grossweiner, L.I, and Kepka, A.G., Photosensitization in Biopolymers, Photochemistry and Photobiology, 1972, pp. 305–314, vol. 16, Pergamon Press, Great Britain.

Wang, Xing, et al., Uptake of Sensitizer by Electroporated Yeast Cells, Bioelectrochemistry and Bioenergetics, 1998, pp. 175–177, vol. 47, Elsevier Sciences S.A.

Wood, Marcia et al., Spinosad Battles Crop Pests, Agricultural Research, Apr. 2000, p. 10, 3p, 5c., vol. 48, U.S. Dept. of Agriculture.

Raloff, Jane, The Bitter End, Science News, Jul. 10, 1999, p. 24, 3p, 6c, vol. 156., Issue 2.

Wood, Marcia, Red Dye, Updated Traps, Agricultural Research, Jan. 1996, p. 20, 3p, 5c, vol. 44, Issue 1, U.S. Department of Agriculture.

Dye Fly, Discover, Oct. 1995, p. 30 1/3p, 1c, vol. 16, Issue 10, Walt Disney Magazine Publishing Group.

Green, Monika J., Hill, H. Allen O., Chemistry of Dioxygen, Methods in Enzymology, 1984, pp. 3–22, vol. 105, Academic Press.

Power, Jr., Paul Spray Alternatives Fly, But Not in Florida, dated Oct. 7, 1997, Tampa Tribune.

Meyer, Fred P.a nd Schnick, A Review of Chemicals Used for the Control of Fish Diseases, Reviews in Aquatic Sciences, 1989, pp. 692–710, vol. 1, Issue 4, CRC Press, Inc.

Andrzejewski, Denis and Weisz, Adrian, Rapid Quantification of Hexachlorobenzene in the Color Additives D&C Red Nos. 27 and 28 (Phloxine B) Using Solid–Phase Microextraction and Gas Chromatography–Mass Spectrometry, Journal of Chromatrography A, 1999, vol. 863, pp. 37–46, Elsevier Science B.V.

Schnick, Rosalie A., The Impetus to Register New Therapeutics for Aquaculture, The Progressive Fish–Culturist, 1988, pp. 190–196, vol. 50.

McBride, Judy Corn Rootworms Get Juiced, Agricultural Research, May 1998, p. 11(1), vol. 46.

Foote, C.S., Denny, R.W. et al., Quenching of Singlet Oxygen, Annals New York Academy of Sciences, 1970, pp. 139–148, vol. 171.

Spikes, John D. and MacKnight, Martha L., Dye–Sensitized photoxidation of Proteins, Annals New York Academy of Sciences, 1970, pp. 149–162, vol. 171.

Gutter, Bezaiei et al., Light–Induced Mutagenicity of Neutral Red (3–Amino–7–Dimethylamino–2–Methylphenazine Hydrochloride), Cancer Research, Apr. 1977, pp. 1112–1114, vol. 37.

Bellin, J.S. and Grossman, L.I, Photodynamic Degradation of Nucleic Acids, Biochemistry and Photobiology, 1965, pp. 45–53, vol. 4, Pergamon Press Ltd., Great Britain.

Griffin, B.R. The Status of Aquaculture Chemicals and Drugs for Disease Control, Aquaculture Magazine, Jan./Feb. 1999, pp. 78–80.

Klaasen, Curtis D., Comparison of the Toxicity of Chemicals in Newborn Rats to Bile Duct–Ligated and Sham–Operated Rats and Mice, Toxicology and Applied Pharmacology, 1973, pp. 37–44, vol. 24, Academic Press, Inc.

Upshall, D.G., Effects of o–Chlorobenzylidene Malononitrile (CS) and the Stress of Aerosol Inhalation Upon Rat and Rabbit Embryonic Development, Toxicology and Applied Pharmacology, 1973, pp. 45–59, vol. 24, Academic Press, Inc.

Linden, Shwn Meei and Neckers, D.C. Type I and Type II Sensitizers Based on Rose Bengal Onium Salts, Photochemistry and Photobiology, 1988, pp. 543–550, vol. 47, No. 4, Pergamon Press plc, Great Britain.

Pimprikar, G.D. et al., Toxicity of Xanthene Dyes to Larvae of Culex Pipiens L. and Aedes Triseriatus S. and Predatory Fish, Gambusia Affinis, The Southwestern Entomologist, Jun. 1984, pp. 218–222, vol. 9, No. 2.

Janovska, Eva et al., On the Nature of Reparable and Non–Reparable Lethal Damage in *E. coli* and Bacteriophage Induced by the Photodynamic Action of Acridine Orange, Int. J. Radiat. Biol., 1970, pp. 317–329, vol. 18, No. 4.

Aquaculture Drug Use: Answers to Commonly Asked Questions, Presented at the FDA Workshop—Requirements for Investigational New Animal Drugs Eastern Fish Health Group and the American Fisheries Society Fish Health Section, Auburn, Alabama, Jun. 19, 1992, Center for Veterinary Medicine, U.S. Food & Drug Administration, published at http://ww.fda.gov/cym/fda/infores/other/aqua/appendixb.html.

Pimprikar, G.D. et al., Toxicity of Xanthene Dyes to Larvae of Culex Pipiens L. and Aedes Triseriatus and Predatory Fish, Gambusia Affinis, The Southwestern Entomologist, Jun. 1984, pp. 218–220, vol. 9, No. 22.

Blazek, E.R. and Hariharan, P.V., Alkaline Elution Studies of Hematoporhyrin–Derivative Photosensitized DNA Damage and Repair in Chinese Hamster Ovary Cells, Photochemistry and Photobiology, 1984, pp. 5–13, vol. 40, No. 1, Pergamon Press, Ltd., Great Britain.

Jefford, Charles W. and Boschung, Andre F., The Dye–Sensitized Photo–Oxygenation of Biadmantylidene, Tetrahedron Letters No. 51, 1976, pp. 4771–4774, Pergamon Press, Ltd., Great Britain.

Ishibashi, Tetsuya et al., Skeletal Sarxoplasmic Reticulum Dysfunction Induced by Reactive Oxygen Intermediates Derived from Photoactivated Rose Bengal, The Journal of Pharmacology and Experimental Therapeutics, 1996, pp. 350–358, vol. 277, American Society of Pharmacology & Experimental Therapeutics, U.S.

Paczkowski, B. et al., Properties of Rose BengalL (X) New Derivatives of Polymer–Rose Bengal, Photochemistry and Photobiology, 1985, pp. 603–604, vol. 42, No. 5, Pergamon Press, Ltd., Great Britain.

Koizumi, Masao, Fundamental Aspects of the Oxidative and Reductive Photobleaching of Xanthene and Thiazine Dyes, Mol. Potochem, 1972, pp. 57–92, vol. 4(1), Marcel Dekker, Inc.

Luttrull, David K. et al., Rose Bengal Aggregation in Rationally Synthesized Dimeric Systems, Photochemistry and Photobiology, 1988, pp. 551–557, vol. 47, No. 4, Pergamon Press, Ltd., Great Britain.

Hardin, Ben, Fruit Fly Dyeing Continues Overseas, Dec. 8, 1997.

Heitz, James, SureDyeô: A Successful Partnership Between the USDA, CDFA and PhotoDye International, Inc., 1998, PhotoDye International, Inc., published at http://ww.suredye.com/news16.html.

Hong–Seok–In and Pyun, Yu–Ryang, Abstract for Membrane Damage and Enzyme Inactivation of Lactobacillus Planatrum by High Pressure $CO_2$ Treatment, International Journal of Food Microbiology, Jan. 22, 2001, pp. 19–28, vol. 63, Issues 1–2, Elsevier Science B.V.

Shin, H.J. et al., Abstract for Eosin Interaction of Alpha–Synuclein Leading to Protein Self–Oligomerization, Biochimica et Biophysica Acta, Aug. 31, 2000, pp. 139–146, vol. 1481, Issue 1.

Andrzejewski, Denis and Weisz, Adrian, Abstract for Rapid Quantification of Hexachlorobenzene in the Color Additives D&C Red Nos. 27 and 28 (Phloxine →B) Using Solid–Phase Microextraction and Gas Chromatography–Mass Spectrometry, Journal of Chromatography A, Nov. 19, 1999, pp. 37–46, vol. 863, Issue 1, Elseview Science B.V.

Hu, X.P. et al., Abstract for Toxicity and Residual Effectiveness of Insecticides on Insecticide–Treated Spheres for Controlling Females of Rhagoletis Pomonella (Diptera: Tephritidae), Journal of Economic Entomology, Apr. 2000, pp. 403–411, vol. 93, Issue 2.

Alcantara–Licudine, J.P. et al., Abstract for Dissipation of Phloxine →B and Uranine in Protein Bait Sprayed in a Coffee Field for the Suppression of Mediterranean Fruit Fly, Bulletin of Environmental Contamination and Toxicology, Mar. 1999, pp. 344–351, vol. 62, Issue 3.

Tonogai, Y. et al., Abstract for Studies on the Toxicity of Coal–Tar Dyes. I. Photodecomposed Products of Four Xanthene Dyes and Their Acute Toxicity to Fish, The Journal of Toxicological Sciences, May 1979, pp. 115–125, vol. 4, Issue 2.

Seno, M. et al., Abstract for A Teratogenicity Study of Phloxine →B in ICR Mice, Food and Chemical Toxicology: an International Journal Published for the British Industrial Biological Research Association, Jan. 1984, pp. 55–60, vol. 22, Issue 1.

Maus, K.L. et al., Abstract for Absence of Mutagenicity of Phloxine →B in *Escherichia Coli* and in *Salmonella Typhimurium*, Mutation Research, Jul.–Sep. 1981, pp. 315–320, vol. 91, Issue 4–5.

Haveland–Smith, R.B. et al., Abstract for Studies on the Genotoxicity of Some Fluorescein Dyes, Mutation Research, Jan. 1981, pp. 1–15, vol. 88, Issue 1.

Ito, A. et al., Abstract for Tumorigenicity Study of (FR 104) in B6C3F1 Mice, Food and Chemical Toxicology: an International Journal of Published for the British Industrial Biological Research Association, Jun. 1994, pp. 517–520, vol. 32, Issue 6.

Tanaka, T., Abstract for Reproductive and Neurobehavioural Effects of Phloxine Administered to Mice, Food and Chemical Toxicology: and International Journal Published for the British Industrial Biological Research Association, Dec. 1993, pp. 1013–1018, vol. 31, Issue 12.

Iwamoto, Y. et al., Abstract for Photodynamic Activities of Food Additive Dyes on the Yeas *Saccharomyces Cerevisiae*, Chemical & Pharmaceutical Bulletin, Jun. 1989, pp. 1632–1634, vol. 37, Issue 6.

Yunker, C.E. et al., Distinctive Staining of Colonies of Cowdria Ruminantium in Midguts of Amblyomma Hebraeum, The Onderstepoort Journal of Veterinary Research, Sep. 1987, pp. 183–185, vol. 54, Issue 3.

Li, Q.X. et al., Abstract for Dissipation of Phloxine →B and Uranine in Sediment and Water at a Kauai Spill Site, Bulletin of Environmental Contamination and Toxicology, Oct. 1998, pp. 426–432, vol. 61, Issue 4.

Mangan, R.L. and Moreno, D.S., Abstract for Photoactive Dye Insecticide Formulations: Adjuvants Increase Toxicity to Mexican Fruit Fly (Diptera: Tephritidae), Journal of Economic Entomology, Feb. 2001, pp. 150–156, vol. 94, Issue 1.

Alcantra–Licudine, J.P. et al., Abstract for Method for Determination of Xanthene Dyes in Guava Fruits and Its Application in a Field of Dissipation Study, Journal of AOAC, International, May–Jun. 2000, pp. 563–568, vol. 83, Issue 3.

Capinera, J.L. and Squittier, J.M., Abstract for Insectidal Activity of Photoactive Dyes to American and Migratory Grasshoppers (Orthoptera: Acrididae), Journal of Economic Entomology, Jun. 2000, pp. 662–666, vol. 93, Issue 3.

Bachmann, A. et al., Abstract for Potent Stimulation and Inhibition of the CFTR CI( . ) Current By Phloxine →B, British Journal of Pharmacology, Oct. 2000, pp. 433–440, vol. 131, Issue 3.

METHOD OF TREATMENT OF PROTOZOAN INFECTIONS IN FISH

RELATED APPLICATION DATA

The present application claims priority from U.S. Provisional Patent Application No, 60/223,915, titled "METHODS OF TREATMENT OF PROTOZOAN INFECTIONS IN FISH", filed on Aug. 9, 2000, the entire contents of which are incorporated by reference herein.

FIELD OF THE INVENTION

The present invention relates to the field of aquaculture. More particularly, the present invention relates to the field of the therapeutic treatment of parasitic infections in fish. More particularly to the use of photoactive dyes such as Phloxine B as a method of controlling protozoan infections in fish populations. More particularly, the invention relates to the use of photoactive dyes such as Phloxine B for the treatment and/or prevention and of parasitic diseases in fish populations such as the disease Ick which is caused by the infection of fish with the external protozoan, *Ichthyophthirius multifiliis*.

BACKGROUND OF THE INVENTION

Aquaculture in the United States represents a relatively small segment of agricultural production, however the industry is relatively young and growing rapidly. Per capita consumption of fish food products in the United States has increased more than 50 percent since 1970. Furthermore, ornamental fish distribution has more than doubled since 1986. Food fish and ornamental fish markets combined contribute nearly $2 billion per year to the retail United-States economy. It has been estimated that these trends will continue in the new millenium.

Although the demand for food fish and ornamental fish products has increased, natural fish harvest populations have not increased and, in many cases, have declined. As such, aquaculture of fish species has increased to meet consumer demand. Among food fish, catfish, salmonid, and cichlid species dominate commercial aquaculture in the US. Catfish aquaculture, estimated at nearly $770 million in farm sales for 1999, accounts for about half of total annual US production. Among ornamental species, guppies, swordtails, and mollies dominate the ornamental fish market in the US. Ornamental aquaculture in Florida alone is valued at over $52 million.

Aquaculture of fish has been plagued by disease since its inception. Disease outbreaks are particularly prevalent when culturing large numbers of fish in crowded conditions. Many parasites and diseases can spread and quickly kill entire fish populations. Although the economic impact of infectious diseases is difficult to determine, it is estimated that annual losses in the US catfish industry may exceed $20 million.

A majority of fish losses in the aquaculture industry can be attributed to protozoan infections. Protozoans can infect both external and internal portions of the fish including the gills, fins, skin, and digestive organs. External protozoa of major concern to aquaculturists include members of the genus Costia, Chilodon, Scyphidia, Trichodina, Epistylis, Carchesium, and Trichophrya. The external ciliate, *Ichthyophthirius multifiliis*, causes white spot disease known as Ick or Ich. Ick is difficult to control and is often observed in crowded cultures of catfish and warm-water aquarium fish. Characteristic signs of Ick infection include the presence of grayish-white warts on the external surfaces of the fish and behavior changes such as flashing, jumping, or thrashing erratically in the water.

The life cycle of *I. multifiliis* is indirect. An adult stage called a trophozoite invades the skin or gills of fish and feeds directly on tissue fluids. Trophozoites, the form of Ick found on fish, are large protozoans and can easily be distinguished by light microscopy. Trophozoites are identified by a clearly visible C-shaped nucleus. After several days, depending on water temperature, the trophozoite releases from the fish, encysts, and undergoes fission to produce the next stage of its life cycle. After the cyst ruptures, an infective form called a tomite is released. As many as 2,000 tomites can be produced from a single cyst. Tomites are highly ciliated, pear-shaped (30–45 nm diameter), and are actively mobile in seeking out a new host. Prior therapeutic efforts to control Ick infections have focused on treating free-swimming tomites and unattached trophozoites. These therapeutic treatments are ineffective in controlling Ick trophozoites once they have attached to the fish.

As of 1999, only five drugs have been approved by the FDA for use in the aquaculture industry. Use of these drugs for particular disease conditions is highly regulated particularly regarding the use of these drugs with food fish. Formalin, oxytetracycline, and sulfadimethoxine have been approved to treat catfish diseases. Although not approved for food fish, potassium permanganate and copper sulfate are also used to treat Ick infections of ornamental fish. Other non-approved drugs, including malachite green and quinine, have been demonstrated effective against Ick. Toxicity and safety concerns have hindered FDA approval of many of these treatments. Malachite green, for example, is both mutagenic and teratogenic, and its use is restricted in many countries. Formalin, although approved, has also been demonstrated as a potential carcinogen to fish. Other drugs, such as potassium permanganate, have been demonstrated to cause gill injury at effective concentrations.

There are arguably no effective long-term treatments for fish infected with the protozoan parasite, *Ichthyophthirius multifiliis*. Prior treatments are ineffective in controlling the complete life cycle of Ick and have the potential to be harmful to fish or other animals, including humans. Current chemical treatments are costly and may also be labor intensive due to clean-up procedures required both before and after treatment. Last, available treatments are not practical for treating large numbers of infected fish such as those cultured in indoor hatcheries or in ponds. Phloxine B, by contrast, is non-toxic to most animal species, does not accumulate or pose an environmental threat, and is relatively inexpensive compared to other drug treatments.

The limited number of approved treatments for protozoan infections results in large production losses each year. Ick alone is responsible for nearly 50% all catfish losses reported during the Spring and Summer months of pond farm production and as mush as 80% of ornamental industry losses annually. The use of Phloxine B for treating Ick infections in fish may dramatically reduce these annual losses. Furthermore, the innovative use of a chemical currently approved by the FDA may reduce the need for extensive environmental and human safety testing before approval.

The limited number of approved and/or effective treatments for Ick infections presents a problem for the aquaculture industry. Costs, however, for approving a single therapeutic by the FDA can typically exceed $50 million. As such, pharmacological suppliers are reluctant to sponsor expensive research and testing campaigns for new drug therapy. Currently, researchers are examining alternative uses for chemicals that have already been FDA approved. For example, oxytetracycline was marketed as a human medicinal and then later approved for use in the aquaculture industry to control certain bacterial infections. Alternative uses for FDA approved chemicals can provide not only an alternative treatment for fish diseases but also reduce the costs associated with extensive FDA research and testing.

Research examining the effectiveness of photodynamic (or photoactive) dyes as pesticides has been conducted since the early seventies. The USDA's Agricultural Research Service (USDA-ARS) have identified at least twenty photodynamic dyes that are toxic to insects, many of which are used in the human cosmetic industry. The pesticide SureDye™ was discovered through a joint effort conducted by the USDA's Animal and Plant Health Inspection Service (USDA-APHIS) and Photodye International, Inc. Specifically, studies demonstrated that Phloxine B, as the active ingredient in SureDye™, was effective in the control of various Diptera species. Other photoactivated dyes such as rose Bengal and acridine orange have been shown to be toxic to fire ants and $E.$ $coli$, respectively. It has been suggested that dye-light therapy may also be effective against the herpes simplex virus.

Phloxine B, is FDA approved and has been used in human cosmetics for nearly 30 years. Phloxine B exists as a powder at room temperature and melts or decomposes at higher temperatures. The compound is a halogenated xanthene dye (see FIG. 1) with a molecular weight of 691.91 g and a water solubility of greater than 120 mg/l.

Due to its hydrophilic nature, bioaccumulation of Phloxine B residues is hypothesized as unlikely. Exposure to sunlight results almost immediate degradation and detoxification (<1 hr), hence the dye is not considered a potential long-term environmental hazard. Metabolites and other degradation products also appear non-toxic. According to the FDA (1982), Phloxine B is relatively non-toxic to humans when ingested ($\leq$1.25 mg/kg body weight). Although potentially a mild skin and eye irritant, the risk of lethal exposure to humans is unlikely. Studies performed on rats, dogs, and mice have also demonstrated the limited adverse effects of Phloxine B ($LD_{50}$ (mg/kg) rat 8400, dog >4600, mouse 310).

The mechanism of action of Phloxine B is not well understood. It has been proposed that the dye collects visible light energy, converting ground state oxygen to a reactive, toxic, single oxygen molecule. Transformation of energy to the short-lived radical results in a series of reactions that eventually result in the formation of a longer-lived, metastable, triplet oxygen molecule. The excess energy of the triplet radical contributes to the oxidation of other chemicals, eventually returning the oxygen to the stable ground state. Photodynamic reactivity of Phloxine B is mediated by several physical and chemical factors including light wavelength and intensity, temperature, pH, and concentration of the dye itself. Because the transfer of light energy to oxygen is facilitated by halogens, the toxicity of the dye directly increases with increasing halogenation.

Studies have demonstrated that photoactive dyes may damage DNA, nucleotides, prokaryotic and eukaryotic cell membranes, viral membranes, and cytosolic proteins. The FDA approved photoactive compound, SureDye™, is administered to insects via food baits. Although the target of toxicity is unknown, researchers suggest that external tissues, not internal organs, are the regions of immediate toxicity. It has been suggested that humans and other animals are protected from the effects of ingesting phototoxic dyes since the internal organs function in relative darkness and, if absorbed, would be rapidly eliminated by the intestines and liver.

SUMMARY OF THE INVENTION

The present Invention comprises the use of photoactive dyes such as Phloxine B, which is chemically known as 2', 4', 5' 7'-tetrabromo-4, 5, 6, 7-tetrachlorofluorescein, disodium salt and which is registered as D&C (Drug and Cosmetic) Red Dye #28, as a treatment for fish infected with external protozoans such as $Ichthyophthirius$ $multifiliis$. It has been discovered that photoactive dyes such as Phloxine B are readily absorbed by external protozoans such as $Ichthyophthirius$ $multifiliis$. It has also been discovered that, after absorption by translucent protozoa such as $Ichthyophthirius$ $multifiliis$, photoactive dyes may be photoactivated by exposing the translucent external protozoa to light. Moreover, it has been discovered that exposure of translucent protozoans to light after absorption of photoactive dyes such as Phloxine B is toxic to the protozoan, presumably due to photoactivation of the photoactive dye.

There are many advantages over the prior art of using photoactive dyes such as Phloxine B as a treatment for fish infected with external protozoans. For example, photactive dyes such as Phloxine B are non-toxic to most animal species, do not accumulate or pose an environmental threat, and are relatively inexpensive. Moreover, because exposure to sunlight results in almost immediate degradation and detoxification, any long-term environmental hazards are unlikely.

According to one embodiment of the invention, there is disclosed a method of treating protozoan infections in fish including introducing a quantity of photoactive dye, such as Phloxine B, to an aqueous environment containing one or more fish infected with protozoa. According to one aspect of the invention, the method includes introducing under low-light conditions a quantity of photoactive dye to an aqueous environment containing one or more fish infected with protozoa.

According to yet another embodiment of the invention, there is disclosed a method of treating protozoan infections in fish including introducing a quantity of photoactive dye to an aqueous environment containing one or more fish infected with protozoan such that the resulting concentration of the photoactive dye in the aqueous environment is toxic to the protozoan. According to one aspect of the invention, the method includes introducing under low-light conditions a quantity of photoactive dye to an aqueous environment containing one or more fish infected with protozoan such that the resulting concentration of the photoactive dye in the aqueous environment is toxic to the protozoan.

According to yet another embodiment of the invention, there is disclosed a method of treating protozoan infections in fish including the steps of: (a) introducing a quantity of photoactive dye to an aqueous environment containing one or more fish infected with protozoa; and (b) repeating step "(a)" one or more times. According to one aspect of the invention, the method includes the steps of: (a) introducing a quantity of photoactive dye under low-light conditions to an aqueous environment containing one or more fish infected with protozoa; and (b) repeating step "(a)" one or more times.

According to yet another embodiment of the invention, there is disclosed a method of treating protozoan infections in fish including the steps of: (a) introducing a quantity of photoactive dye to an aqueous environment containing one or more fish infected with protozoan such that the resulting concentration of the photoactive dye in the aqueous environment is toxic to the protozoan; and (b) repeating step (a) one or more times. According to one aspect of the invention, the method includes the steps of: (a) introducing a quantity of photoactive dye under low-light conditions to an aqueous environment containing one or more fish infected with protozoan such that the resulting concentration of the photoactive dye in the aqueous environment is toxic to the protozoan; and (b) repeating step (a) one or more times.

According to yet another embodiment of the invention, there is disclosed a method of treating protozoan infections in fish including the steps of: (a) introducing a quantity of photoactive dye under low-light conditions to an aqueous environment containing one or more fish infected with protozoan; (b) allowing sufficient time for protozoan absorption of the photoactive dye under low-light conditions; and (c) photoactivating the absorbed photoactive dye. According to one aspect of the invention, the method includes the steps of: (a) introducing a quantity of photoactive dye under low-light conditions to an aqueous environment containing one or more fish infected with protozoan; (b) allowing sufficient time for protozoan absorption of the photoactive dye under low-light conditions; (c) photoactivating the absorbed photoactive dye; and (d) repeating steps (a)–(c) one or more times.

In accordance with these discoveries, it is an object of the present invention to provide a method for the control of external protozoan in fish populations. Other objects of the present invention will become readily apparent from the following description.

DETAILED DESCRIPTION OF THE INVENTION

Figure 1:
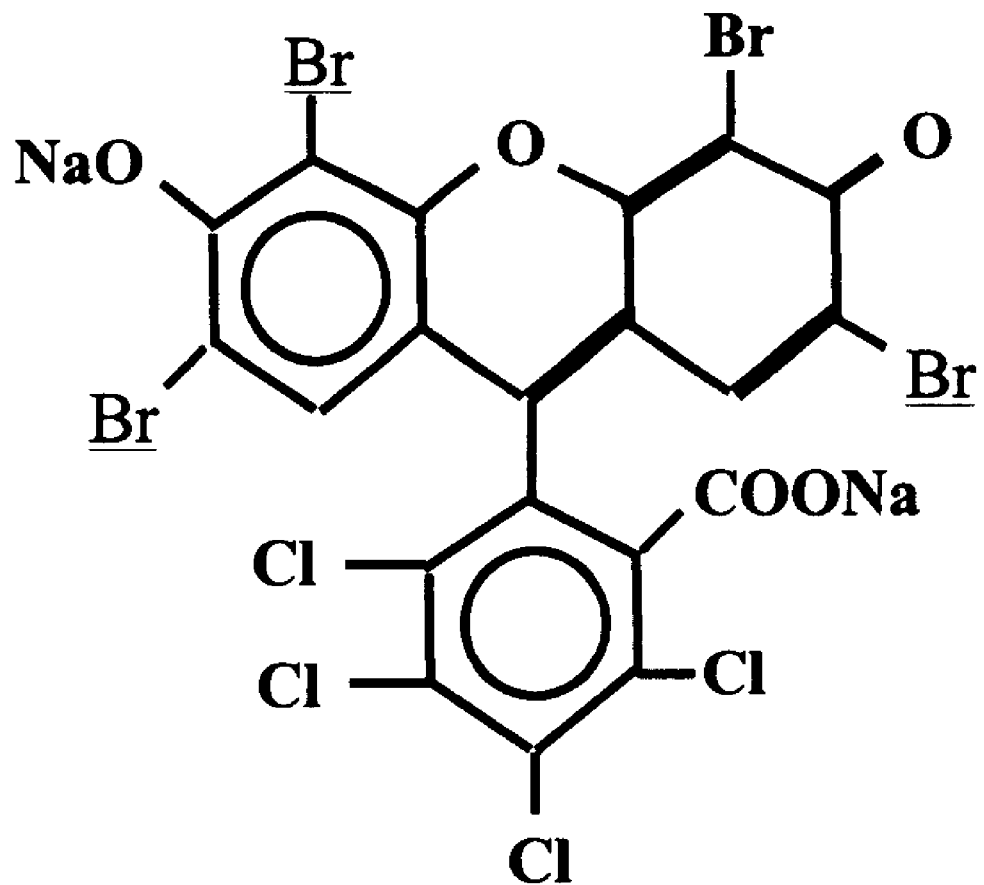
FIG. 1 illustrates the chemical structure of Phloxine B.

The present invention now will be described more fully. This invention may be embodied in many different forms and should not be construed as limited to the embodiments set forth herein; rather, these embodiments are provided so that this disclosure will be thorough and complete, and will fully convey the scope of the invention to those skilled in the art.

Photoactive dyes such as Phloxine B may be readily absorbed by protozoans. Because many protozoans such as *Ichthyophthirius multifiliis* are translucent it is possible to photoactivate the dyes after absorption by the protozoans. Photoactiviation of dyes after absorption by protozoans may be lethal to the protozoans. Therefore, photoactive dyes may be used as an effective treatment for fish infected with external translucent protozoans.

Examples of photoactive dyes which may be used to practice the present invention include, but are not limited to Azure A, Azure B, Methylene Blue, NewMethyleneB1 N, Toluidine Blue, Methylene Green, Thionin, Brilliant Cresylblue, Rhodamine B, Thioflavine T, Eosine Y, Erythrosine B, Phloxine B, Pyronine Y, Rhodamine 6 G, Rose Bengal, D&C Orange 5, Pyronine B, Neutral Red, Safranin O, Auramine O, and Alizarin Red S. Included in this list are several dyes which are used as food, cosmetic, or as dyes for cloth, leather, wool, cotton, and the like, which have been approved by the FDA for use as food, drug, or cosmetic. Those skilled in the art may be aware of other photoactive dyes which could be used to practice the present invention.

By way of example only, the present invention may be practiced by adding a quantity of photoactive dye to an aqueous environment containing a population of fish infected with external translucent protozoans. The photoactive dye may be added to the aqueous environment in a dry powdered form or as a liquid, such as from a stock solution of known concentration. A single species of photoactive dye may be added to the aqueous environment or combinations of different photoactive dyes may be used. For example, SureDye™, which is composed of a 1:1 molar mixture of Phloxine B (D&C Red Dye No. 28–69% by weight) and Uranine (D&C Yellow Dye No. 8–31% by weight), may be used.

The photoactive dyes are preferably introduced to the aqueous environment under low light conditions. Low light conditions may be necessary to prevent substantial deactivation or degradation of the photoactive dyes prior to absorption by the protozoans. In a preferred embodiment, the photoactive dye is added to the aqueous environment at night-time.

In a preferred embodiment, after addition of the photoactive dye to the aqueous environment, sufficient time should be provided to allow the protozoans to absorb the photoactive dye before exposure to light. In a preferred embodiment, the photoactive dye is added at night and the protozoans are allowed to uptake the dye over a period of several hours before exposure to daylight.

After the photoactive dye is absorbed by the external, translucent protozoans, the protozoans are exposed to light. Presumably, as a result of the photoactivation of the absorbed dye, those protozoan which have absorbed the photoactive dye and are exposed to light will be killed.

The effectiveness of treatments of photoactive dyes on parasite control in a particular fish population can be determined by those skilled in the art by monitoring the general behavior of the fish (swimming, feeding, etc.) and the appearance of the parasite by microscopic examination. For example, live Ick trophozoites may be monitored using image analysis microscopy using a Image-Pro Plus V. 4.0.0.13, available from Media Cybernetics, L.P.

In one embodiment of the invention, the photoactive dye, Phloxine B, is added as a dry powder to an aquarium containing fish infected with Ick. The Phloxine B is added to achieve a final concentration of around 5 mg/L. The Phloxine B is added to the aquarium in darkness and at least eight hours of absorption is allowed before photoactivation. Photoactivation is achieved by exposing the Ick infected fish to light from artificial lamps. Microscopic examination suggests that Phloxine B is effective against the formerly invulnerable trophozoite stage when attached to the fish host. Although this particular embodiment is performed in a laboratory setting, those skilled in the art will understand that the teachings can be adapted to a commercial operation without undue experimentation.

The invention is described further in the following non limiting examples:

EXAMPLE 1

An in vivo study was conducted involving the direct dosing of Ick parasites with Phloxine B. 1 µl of Ick theronts, both free-swimming tomites and non-ruptured cysts, and 9 µl of a Phloxine solution containing either 1000, 100, 10, 1 and 0 ppm of Phloxine B were placed into 100×15 mm tri-plate petri dishes providing 3 replicates for each treatment. 1 set of the plates was left exposed to ambient light (6 mE $m^{-2}s^{-1}$) for 5 hr (LIGHT EXPERIMENT), while the other set was kept in the dark for 4 hr then exposed to ambient light for 1 hr (DARK EXPERIMENT). Percent mortality was assessed, then both light and dark plates received a second dose of Phloxine B at the same concentration as before and treated in the same manner. The results of the experiment are shown in the tables below:

| LIGHT EXPERIMENT (Ambient Light) | | |
| --- | --- | --- |
| Phloxine B TREATMENT | 1 DOSE | 2 DOSES |
| 1 ppm | No effect | No effect |
| 10 ppm | No effect | No effect |
| 100 ppm | 20% Mortality | 80% Mortality |
| 1000 ppm | 80% Mortality | 100% Mortality |

| DARK EXPERIMENT (Lab Conditions) | | |
| --- | --- | --- |
| Phloxine B TREATMENT | 1 DOSE | 2 DOSES |
| 1 ppm | No effect | No effect |
| 10 ppm | No effect | No effect |
| 100 ppm | No effect | 10% Mortality |
| 1000 ppm | 40% Mortality | 95% Mortality |

EXAMPLE 2

A light and dark experiment were set up following the protocol in Example 1, but exposure times were doubled—8 hr dark then 2 hr light or 10 hr light. The results indicated that longer exposure time increased the effectiveness of the dye.

EXAMPLE 3

An experiment was designed to test the effect of light intensity on the effectiveness of Phloxine B treatment of Ick. The previous experiments described in Examples 1 and 2 were conducted in the lab. The ambient light intensity in the lab was very low, 6 $\mu$mol m$^{-2}$s$^{-1}$. An experiment was conducted as following the protocol of Example 1, except the experiment was conducted in a greenhouse to better mimic natural light conditions. The results from the Light Experiment under Greenhouse conditions are shown in the table below:

| LIGHT EXPERIMENT (Greenhouse Conditions) | |
| --- | --- |
| TREATMENT | 1 DOSE |
| 1 ppm | No effect |
| 10 ppm | No effect |
| 100 ppm | 50% Mortality |
| 1000 ppm | 100% Mortality |

Conclusions drawn from the experiments described in the Examples 1–3 above were that increased exposure time and increased light intensity both increased the effectiveness of the Phloxine B dye as a treatment for Ick. At low light intensities, multiple doses also increased the dye's effectiveness. It was also observed that the dye was taken up both free-swimming and encysted organisms.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of treating infections in fish comprising: introducing a sufficient quantity of one or more photoactive dyes to an aqueous environment containing protozoa so that the resulting concentration of photoactive dye in the aqueous environment is toxic to at least a portion of the protozoa when the photoactive dye is photoactivated by exposure to light.

2. The method of claim 1 wherein introducing a sufficient quantity of one or more photoactive dyes comprises introducing Phloxine B.

3. The method of claim 2 wherein introducing Phloxine B comprises introducing Phloxine B so that the resulting concentration of Phloxine B in the aqueous environment is between 5 parts per million and 20 parts per million.

4. The method of claim 1 wherein introducing a sufficient quantity of one or more photoactive dyes comprises introducing the sufficient quantity of one or more photoactive dyes to the aqueous environment under low-light conditions.

5. The method of claim 4 wherein introducing a sufficient quantity of one or more photoactive dyes comprises introducing Phloxine B.

6. The method of claim 5 wherein introducing Phloxine B comprises introducing Phloxine B so that the resulting concentration of Phloxine B in the aqueous environment is between 5 parts per million and 20 parts per million.

7. A method of treating infections in fish comprising the steps of:
   (a) introducing a sufficient quantity of one or more photoactive dyes to an aqueous environment containing protozoa so that the resulting concentration of the photoactive dye in the aqueous environment is toxic to at least a portion of the protozoa when the photoactive dye is photoactivated by exposure to light;
   (b) repeating step (a).

8. The method of claim 7 wherein introducing a sufficient quantity of one or more photoactive dyes comprises introducing Phloxine B.

9. The method of claim 8 wherein introducing Phloxine B comprises introducing Phloxine B so that the resulting concentration of Phloxine B in the aqueous environment is between 5 parts per million and 20 pars per million.

10. The method of claim 7 wherein introducing a sufficient quantity of one or more photoactive dyes comprises introducing the sufficient quantity of one or more photoactive dyes to the aqueous environment under low-light conditions.

11. The method of claim 10 wherein introducing a sufficient quantity of one or more photoactive dyes comprises introducing Phloxine B.

12. The method of claim 11 wherein introducing Phloxine B comprises introducing Phloxine B so that the resulting concentration of Phloxine B in the aqueous environment is between 5 parts per million and 20 parts per million.

13. A method of treating infections in fish comprising the steps of:
   (a) introducing under low-light conditions a sufficient quantity of one or more photoactive dyes to an aqueous environment containing protozoa so that the resulting concentration of photoactive dye in the aqueous environment when photoactivated by exposure to light is toxic to at least a portion of the protozoa;

(b) after allowing sufficient time for at least a portion of the protozoa to absorb at least some of the photoactive dye under low-light conditions, photoactivating the photoactive dye by exposure to light.

14. The method of claim 13 wherein introducing a sufficient quantity of one or more photoactive dyes comprises introducing Phloxine B.

15. The method of claim 14 wherein introducing Phloxine B comprises introducing Phloxine B so that the resulting concentration of Phloxine B in the aqueous environment is between 5 pats per million and 20 parts per million.

16. The method of claim 13, further comprising repeating steps (a)–(b).

17. The method of claim 16 wherein introducing a sufficient quantity of one or more photoactive dyes comprises introducing Phloxine B.

18. The method of claim 17 wherein introducing Phloxine B comprises introducing Phloxine B so that the resulting concentration of Phloxine B in the aqueous environment is between 5 parts per million and 20 parts per million.

* * * * *

UNITED STATES PATENT AND TRADEMARK OFFICE
Certificate

Patent No. 6,506,791 B2                                Patented: January 14, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Benjamin G. Blair, Ohatchee, AL; and Mark E. Meade, Jacksonville, AL.

Signed and Sealed this Tenth Day of February 2004.

SREENI PADMANABHAN
*Supervisory Patent Examiner*
Art Unit 1617

UNITED STATES PATENT AND TRADEMARK OFFICE
CERTIFICATE OF CORRECTION

PATENT NO. : 6,506,791 B2
DATED : January 14, 2003
INVENTOR(S) : Blair

It is certified that error appears in the above-identified patent and that said Letters Patent is hereby corrected as shown below:

Title page,
Item [75] Inventor, insert -- Mark E. Meade, Jacksonville, AL (US) --.
Item [56], References Cited, OTHER PUBLICATIONS,
"N. Houba-Herin et al." reference, before "and" insert -- Oxidation --;
"Heitz, James R." reference, "Halogenated Xanthene" should read -- Photoactivated --;
"Hatch, Audrey C." reference, cancel "on Fluoranthene" ;
"Carpenter, Terry L." reference, "American" should read -- America --.
"Walthali, W.K. and Stark, J.D.," reference, "Walthali" should read -- Walthall --.
"Rayburn, James R. et al.," reference, "Amininicotinamide" should read
-- Aminonicotinamide --;
"Walthali, W.K. and Stark, J.D.," reference, "Walthali" should read -- Walthall --.
"Meyer, Fred P." reference, "a nd" should read -- and --;
"Aquaculture Drug Use:" reference, "ww" should read -- www --;
"Paczkowski, B. et al." reference, "Paczkowski" should read -- Paczkowska --; "BengalL"
should read -- Bengal:
"Heitz, James" reference, "ww" should read -- www --.
"Ito, A. et al." reference, after "Journal" cancel "of";
"Capinera, J.L." reference, "Squittier" should read -- Squitier --;
"Bachmann, A. et al.," reference, "(.)" should read -- (-) --.

Column 8,
Line 47, "pars" should read -- parts --.

Column 9,
Line 11, "pats" should read -- parts --.

Signed and Sealed this

Eleventh Day of May, 2004

JON W. DUDAS
*Acting Director of the United States Patent and Trademark Office*